United States Patent [19]
Khalil

[11] 4,217,910
[45] Aug. 19, 1980

[54] INTERNAL JUGULAR AND LEFT VENTRICULAR THERMODILUTION CATHETER

[75] Inventor: Hassan H. Khalil, Alexandria, Egypt

[73] Assignee: The United States of America as represented by the Secretary of the Navy, Washington, D.C.

[21] Appl. No.: 949,912

[22] Filed: Oct. 10, 1978

[51] Int. Cl.² ............................................. A61B 5/02
[52] U.S. Cl. ..................................... 128/670; 73/204; 128/642; 128/692; 128/713
[58] Field of Search ............... 128/670, 692, 713, 642; 73/204

[56] References Cited

U.S. PATENT DOCUMENTS

| | | | |
|---|---|---|---|
| 3,075,555 | 1/1963 | Richards | 128/692 |
| 3,359,974 | 12/1967 | Khalil | 128/713 |
| 3,438,253 | 4/1969 | Kuether et al. | 73/244 |
| 3,478,588 | 11/1969 | Richardson | 73/362 |
| 3,595,079 | 7/1971 | Grahn | 73/204 |
| 3,623,364 | 11/1971 | Withrow | 73/204 |
| 3,722,505 | 3/1973 | Kolin | 128/692 |
| 3,734,083 | 5/1973 | Kolin | 128/692 |
| 3,789,831 | 2/1974 | Kopaniky et al. | 128/692 |
| 3,798,967 | 3/1974 | Gieles et al. | 73/204 |
| 3,995,623 | 12/1976 | Blake et al. | 128/642 |

OTHER PUBLICATIONS

*The Lancet,* Jun. 22, 1963, p. 1352.
*Journ. of Applied Physiol.,* vol. 21, 1966, p. 1131.
*World Conf. on Schistosomiasis Symposium,* Oct. 1975, paper by Khalil, H. H., pp. 1–20.
*Circulation Research,* vol. X, Mar. 1962, Hosie, K. F.
*American Heart Journ.,* vol. 83, No. 3, Mar. 1972, p. 306.

*Primary Examiner*—Kyle L. Howell
*Attorney, Agent, or Firm*—Richard S. Sciascia; W. Thom Skeer; T. R. Schulte

[57] ABSTRACT

A thermodilution catheter having a distal high frequency heating coil of fine wires, heat measuring thermocouples, and a proximal resistance thermometer, all wound externally on a catheter for measuring blood flow in either the jugular vein or the left ventricle of the heart. The device also incorporates electrodes for electrocardiogram tracings.

11 Claims, 4 Drawing Figures

INTERNAL JUGULAR AND LEFT VENTRICULAR THERMODILUTION CATHETER

BACKGROUND OF THE INVENTION

1. Field of the Invention

The invention pertains to the field of biomedical instrumentation. By way of further explanation, this invention pertains to the electronic instrumentation of the cardiovascular system of a living organism. In still greater particularity the invention provides simultaneous indications of a plurality of cardiovascular conditions. This invention is further characterized by its use of thermodilution techniques to provide an indication of the quantity of blood flow in the cardiovascular system. Additionally this invention can provide an intracardiac electrocardiogram tracing.

2. Description of the Prior Art

Thermodilution is an application of the calorimetric principle that, in a mixture of fluids at different temperatures, the heat lost by one fluid equals the heat gained by the other. For each fluid, the mathematical product of the temperature change, specific heat and mass is equal.

A recognized method for the study of blood circulation involves producing a temperature change in the blood at one point in the blood flow and measuring the temperature change at a second downstream point. Assuming that the measurement of the temperature change occurs at a point downstream of the heat source and that the blood's heat content is uniform, the measured change will reflect the amount of blood passing through the blood vessel.

In thermodilution studies heat is either removed from or added to the blood stream. One technique involves the injection of a slightly cooler saline solution into the blood. It was introduced by Gegler in 1953 and involved the injection of cold blood or Ringer's solution and measurement of temperature in the pulmonary artery or aorta with thermocouples. The resulting temperature time curve resembled the previously used dye dilution methods of measuring cardiac output. However, this method requires an accurate measurement of the mass and temperature of each injection.

Methods of introducing heat to the blood flow itself have been developed. For example, in U.S. Pat. No. 3,438,253 issued to Frederick W. Kuether et al. on Apr. 15, 1969, a catheter with a heating coil of platinum ribbon, whose resistance changes with temperature, is described. By measuring the energy required to maintain the coil at a constant, elevated temperature, the velocity and direction of blood flow may be determined. While satisfactory for its intended purpose, this device uses continuous heating which could raise the overall temperature of the blood thus reducing accuracy. Furthermore, it is required to measure the cross sectional area of the vessel, which changes during each systole and diastole, and multiply the "velocity" by the cross section of the vessel to obtain volume flow. The velocity of fluid inside the vessels follows a parabolic function (Ruch & Fulten, Medical Physiology & Biphysics p. 248) and therefore the velocity obtained will depend on the position of the catheter inside the vessel and will change with any movement of the catheter to or from the center of the vessel.

In some devices, thermistors, or thermally sensitive resistors, composed of an oxidic semiconductive material whose resistance varies with temperature, are employed as temperature measuring devices. A Wheatstone Bridge is used to measure resistance change in the sensing element. This temperature sensing resistance-element is used as one arm of the bridge. If the other three resistance arm values are known, and the bridge is balanced, then there is no current through the galvanometer and the fourth resistance is easily calculated. Once the resistance value of the thermally sensitive resistor is known then the actual temperature is calculated.

Another heating method involves the introduction of heat at one point in the blood flow and the measurement of blood temperature at a downstream point. A device utilizing this method is shown in U.S. Pat. No. 3,359,974, issued to Hassan H. Khalil on Dec. 26, 1967. This device uses a standard bilumen or trilumen cardiac catheter tube, about 3 mm dia., with fine lead wires connected to a heater winding, and a distal temperature transducer to measure the temperature change.

The heater winding is 12 to 15 cm of six fine enameled constantan wires, 0.04 mm dia. wound in parallel and soldered to the flattened tip of a lead wire as it emerges from a lumen of the catheter. The coil is heated with high frequency (350 khz) current in order not to excite the myocardium. The temperature transducer is a fine nickel or platinum resistance thermometer in the form of a bifilar winding over the distal 16 cm of the catheter. The windings are covered with a thin layer of flexible varnish. The temperature transducer is connected to a three-lead thermometer bridge and a D.C. amplifier and recorder.

The catheter is designed so that the heating coil will be in the right atrium and superior vena cava and the temperature transducer will lie in the pulmonary artery. While satisfactory for its intended purposes long areas of windings are necessary to eliminate errors introduced through incomplete blood mixing and laminar flow. In addition, the temperature sensing unit is located on the distal or tip portion of the catheter. This only allows for insertion of the catheter in the same direction as the blood flow.

SUMMARY OF THE INVENTION

The invention is a miniature thermodilution catheter for use in the internal jugular vein or a normal size thermodilution catheter for measurement of left ventricular output. This catheter is used where it is desired or required to introduce the catheter against the blood flow as, for example, if it is desired to meausre internal jugular blood flow. The upstream high frequency heating coil is distally located at the tip of the catheter and the downstream platinum resistance thermometer is proximally located on the catheter so as to measure blood temperature before any tributaries enter the vein.

Fine lead wires are wound on the outside of the catheter and connected at solder points to the heating coil, which consists of six constantan wires for the internal jugular vein and 9 constantan wires for the left ventricle, bifilarly wound onto the catheter. The downstream resistance thermometer is also bifilarly wound. A thermocouple measures local temperature rise at the heating coil and is connected in series with a reference thermocouple, located between the heating coil and resistance thermometer. In addition, electrodes are included on the catheter so that electrocardiogram tracings may be made.

DESCRIPTION OF THE PREFERRED EMBODIMENT

Figure 1:
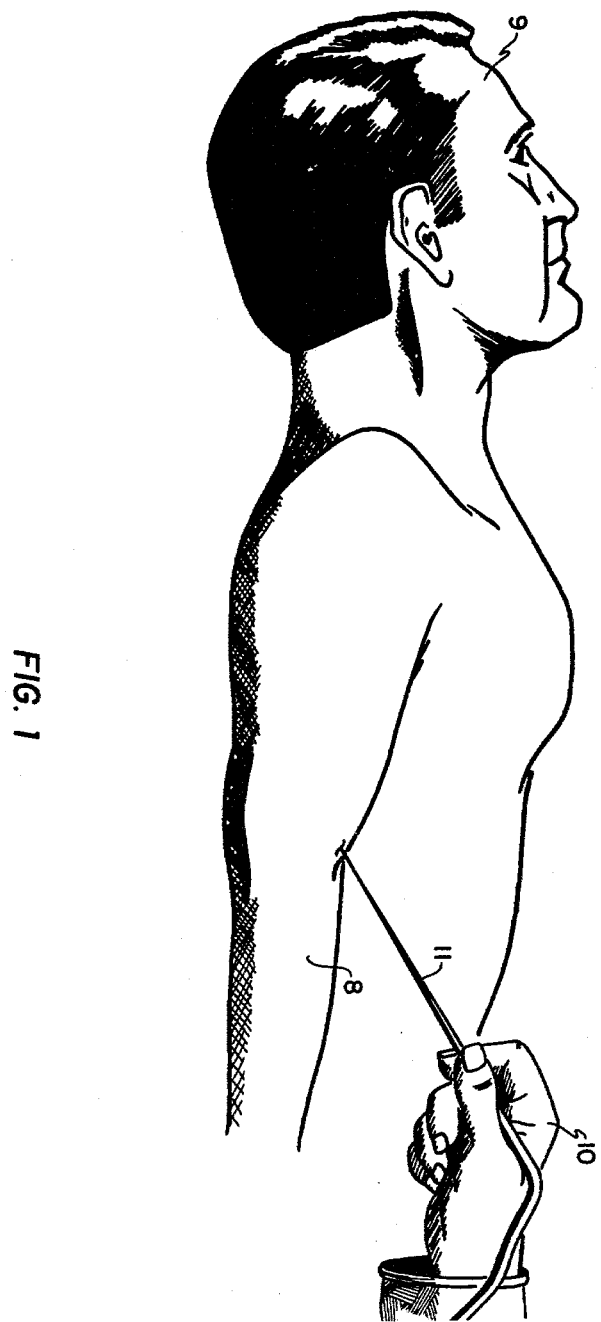
FIG. 1 is a perspective view showing the invention being used to measure internal jugular flow.

Referring to FIG. 1, catheter 11 is inserted into living organism 9 by operator 10 through one of the tributaries of the antecubital veins at elbow 8. Catheter 11 is then passed upwards to the neck of living organism 9 and guided manually under screening into the internal jugular vein. Left ventricular catheters are introduced through one of the femoral arteries.

Figure 2:
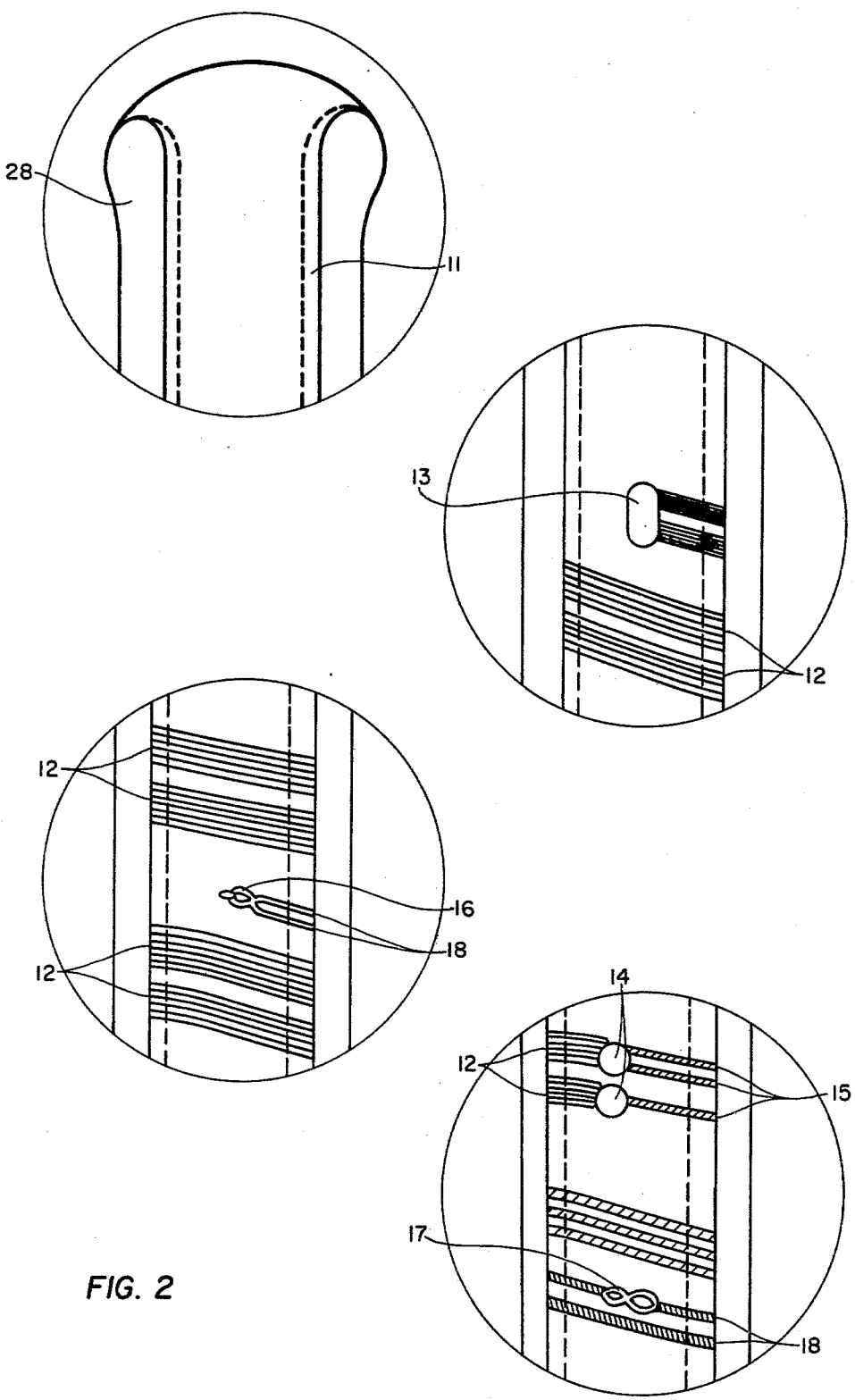
FIG. 2 is a segmented view of the distal or tip portion of the catheter.

Referring to FIG. 2, the invention is built upon catheter body 11 which is preferably 1.5 mm in diameter if used to measure venous blood flow, and about 2.6–2.8 mm if used to measure left ventricular output. Heating coil 12 is composed of 2 windings each of six to nine strands of fine constantan wires bifilarly wound onto the distal portion of catheter 11. The two wire windings are joined on the distal portion at solder point 13. Heating coil 12 terminates proximally in solder points 14 from which 3 lead wires 15 emanate.

Between heating coil windings 12 a copper constantan thermocouple 16 is affixed to catheter 11. Lead wires 18 connect thermocouple 16 in series with reference copper constantan thermocouple 17 located proximally of the heating coil. These thermocouples provide a convenient measure of the local temperature rise at the heating coil 12.

Figure 3:
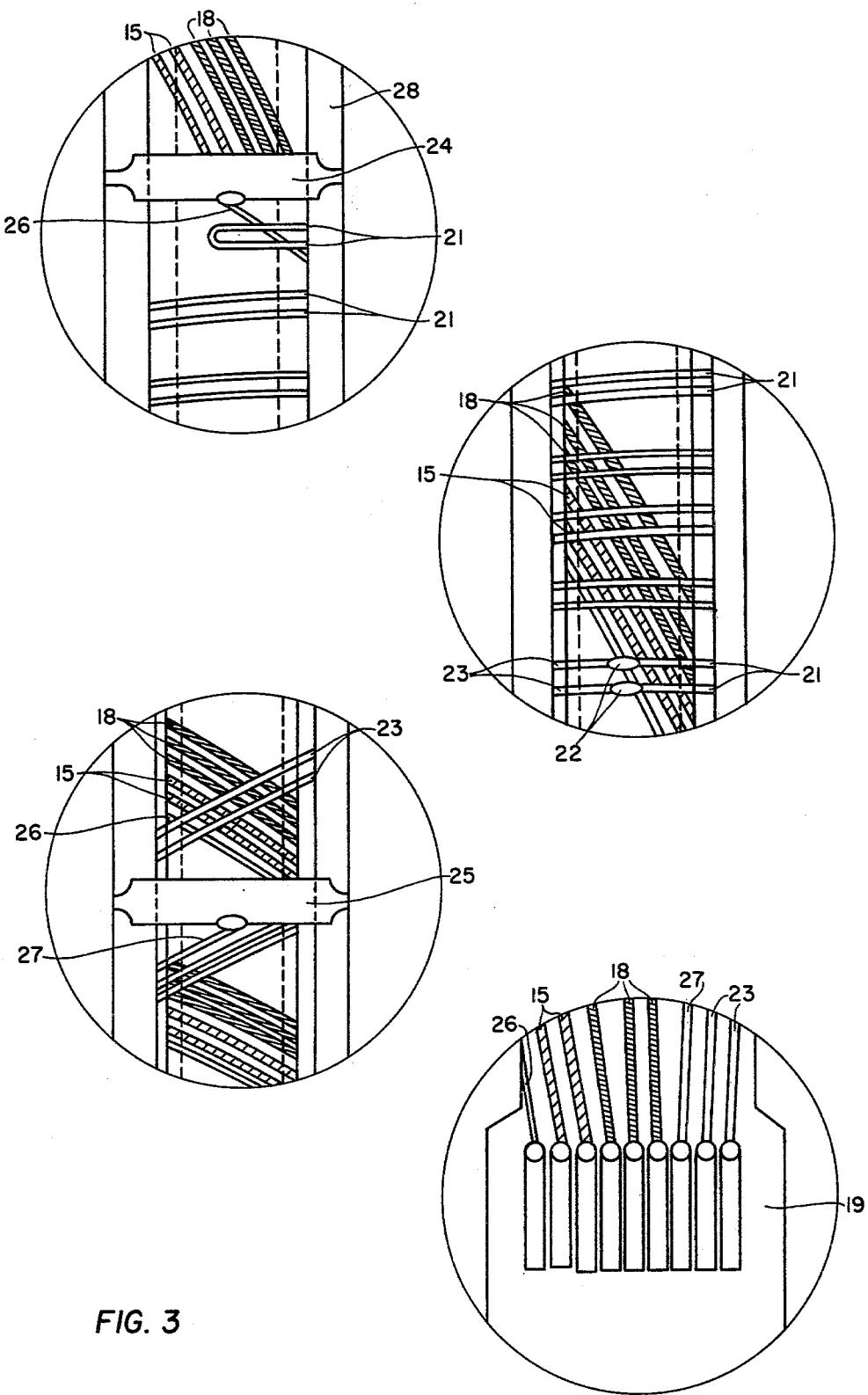
FIG. 3 is a segmented view of the base plug and the portion of the catheter proximal to the heating coil.

Referring to FIG. 3, lead wires 15 and 18 are wound on catheter 11 and terminate in plug 19. Platinum resistance thermometer 21 is bifilarly wound onto catheter 11. Thermometer 21 terminates in solder points 22 from which lead wires 23 emanate. Lead wires 23 terminate at plug 19.

On opposite sides of resistance thermometer 21, bare platinum electrodes 24, 25 are provided for electrocardiogram tracings. Electrode 24 has lead wire 26 terminating in plug 19. Electrode 25 has lead wire 27 terminating in plug 19. Plug 19 connects the catheter assembly to the electronics necessary to obtain the thermodilution measurements.

Catheter body 11, which is a flexible, woven body, along with the rest of the above-described apparatus, is covered with inert plastic coating 28 which is applied in 3 layers after winding the wires. Multiple layers ensure perfect electric insulation. The plastic is diluted with ethyl acetate to make each layer thinner. A layer of inert plastic coating is also placed on the inside of catheter 11. Silicone rubber may be used as the inert coating.

Figure 4:
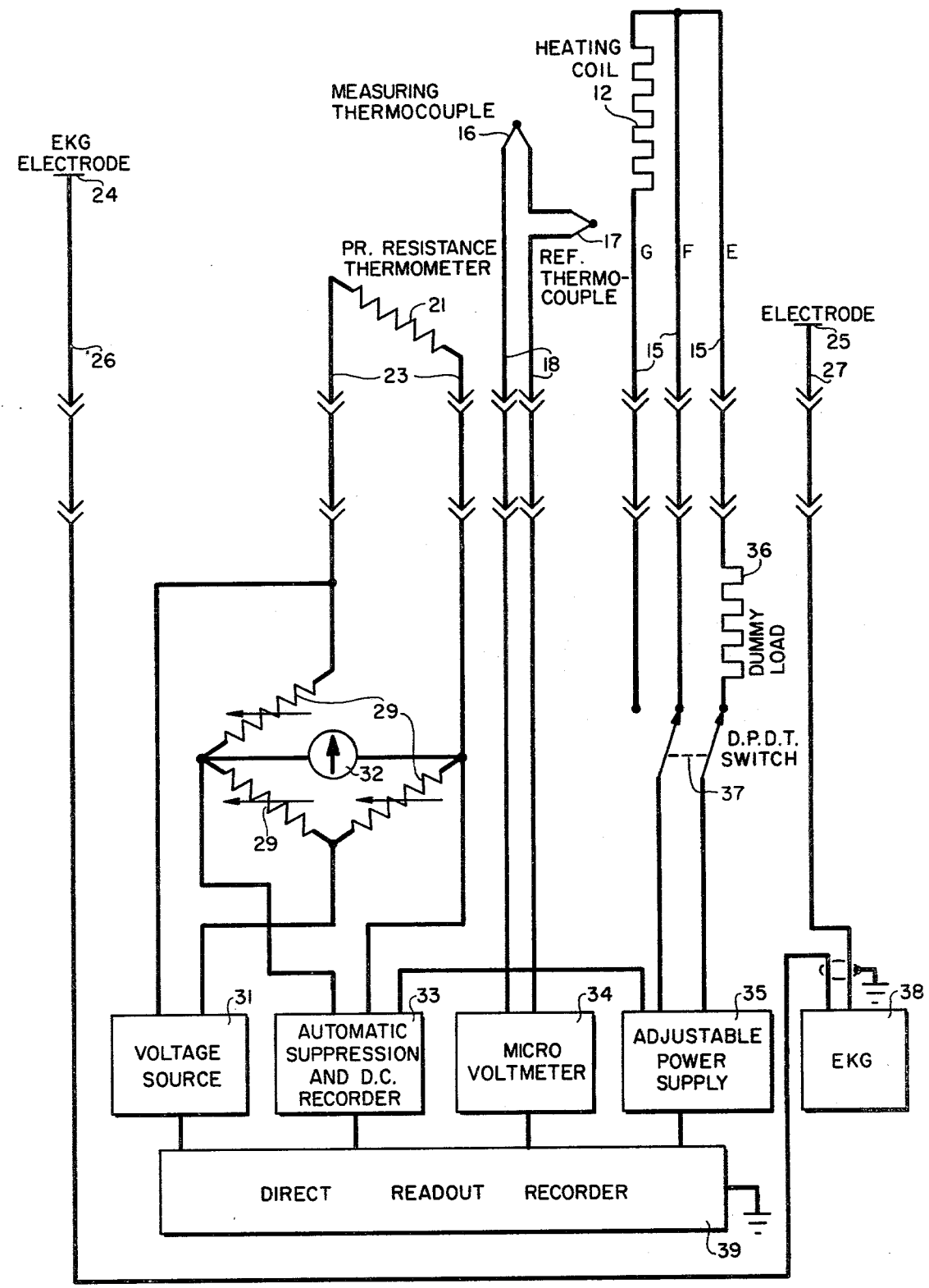
FIG. 4 is a schematic representing the electronic aspects of the invention.

Referring to FIG. 4, platinum resistance thermometer 21 is one arm of a Wheatstone Bridge. Standard voltage source 31, which may be for example, a 1.35 V mercury battery, galvanometer 32, automatic balance and D.C. recorder 33 and three variable resistors 29 complete the bridge. Two leads 23 are used to connect thermometer 21 to variable resistors 29. Thermometer 21 thus forms one arm of the bridge. Temperature changes down to 0.001° C. can be detected using this configuration.

Thermocouples 16 and 17 located on the catheter in the heating coil region are connected to microvoltmeter 34 by lead wires 18. These temperature transducers permit accurate measurement of temperature differences and thus provide an indication of the local temperature rise at the heating coil 12.

Heating coil 12 is connected to adjustable power supply 35 and external dummy load 36. Double pole-double throw switch 37 selectively supplies power to heating coil 12 or dummy load 36. Dummy load 36 acts as a warming medium for the connecting wiring. The power supply is adjustable so that the rate of heating of the coil may be determined prior to applying power to the catheter. Electrodes 24 and 25 are connected to electrocardiograph 38 by leads 26 and 27 respectively.

Finally, electronic components 31, 34, 35 are electrically connected to direct readout recorder 39.

MODE OF OPERATION

The present invention may be utilized when circumstances prevent insertion of a catheter in the same direction as blood flow. Insertion of a catheter against the blood flow requires that the heating element be upstream at the tip or distal portion of the catheter and that the thermometer be downstream at a more proximal portion of the catheter.

Referring to FIG. 1, to measure internal jugular blood flow, catheter 11 is introduced first in the same direction as the blood stream through one of the tributaries of the antecubital vein at elbow 8. Next, catheter 11 is directed against the blood stream into the internal jugular vein under x-ray screening and an image intensifier, and measurements are obtained when the head of living organism 9 is below the level of the heart. This prevents applying heat while the vein is empty.

Referring to FIG. 2, the heat applied by mean heating coil 12 at a predetermined constant rate need not exceed 6–8 seconds in duration for internal jugular measurements inasmuch as the temperasure rise measured by downstream platinum resistance thermometer 21, reaches the "plateau" of the asymoptote within four seconds. This relatively short heating time reduces the recirculation problem which has affected prior devices and methods. In addition, the capillary bed acts as a very large heat "sink" which also minimizes recirculation problems. The modest mean temperature rise ranges between 0.04° C. and 0.15° C. This rise affects only the volume flow during the period of heating and not the entire minute volume and is therefore not likely to affect heart function or blood vessel intima during or after the measurements.

When the thermometer is located in the venous system and pulmonary arteries, the heating time should be up to 12 seconds in normal individuals. If there is heart failure, then the heating time should be longer because in cases of Rt heart failure the stroke volume is small relative to the residual fraction remaining in the right ventricle after each systole. This is not the case for catheters designed for the internal jugular vein because there is no residual fraction and the flow is continuous, therefore the heating time need not exceed 6–8 seconds.

Referring to FIGS. 2 and 3, lead wires 15, which supply current to heating coil 12, must pass under the proximal resistance thermometer 21 to reach heating coil 12. Since lead wires 15 are heated while current passes through them, a possible source of error is introduced because heat from lead wires 15 will be conducted through catheter wall 11 and resistance thermometer 21 will also be heated.

Referring to FIG. 4, this possible source of error is avoided by placing a dummy load 36, an identical bifilarly wound heating coil, inside the apparatus. Dummy load 36 has an impedance identical to that of heating coil 12 on the distal segment of the catheter. Power is applied to dummy load 36 at all times except during the measuring time. The circuit supplying power to dummy load 36 includes lead wires 15 E and F which pass under resistance thermometer 21 to reach heating coil 12, where they are connected together without supplying any heat to heating coil 12. On applying heat by means of double pole-double throw switch 37 to heating coil 12, lead wire 15 E will be out of the circuit. Therefore either wires 15E and 15F, connected to dummy load 36, or 15F and 15G connected to main heating coil 12, will heat thermometer 21 to an equal degree on applying power either to heating coil 12 or to dummy load 36. The heating of wires 15E, F, and G will therefore not be detected by galvanometer 32 and recorder 39 and will therefore not affect the measurement. Thus, dummy load 36 and switch 37 constitute auxiliary heating means to heat the electrical leads 15.

In the present invention automatic balance and D.C. recorder 33 for balancing the bridge is provided in the design of the electronic apparatus necessary to obtain thermodilution measurements. A predetermined rate of heating can be introduced only after automatic balancing of the bridge is reached. During the balancing time, a push button on the face of direct readout recorder 39 is lit with a sign to "wait". When automatic balancing of the bridge is reached the "wait" light is turned off and another push button with a sign "exp." (exposure) is lit indicating that the electronic circuit is ready to introduce heat. When "exp." button is pushed, the predetermined rate of heating starts and remains on for the predetermined number of seconds and automatic suppression and D.C. recorder 33 is disconnected. On starting "exposure" and throughout the exposure time, the automatic balancing device is cancelled so that the required deflection is obtained. The automatic balancing of the bridge is reactivated after heating time is over.

Referring to FIG. 2, heating coil 12 is made of constantan wires 0.04 millimeters O.D. Referring to FIG. 3, resistance thermometer 21 is made of 99.99% pure platinum wires 0.02-0.03 millimeters O.D. All of the wires in heating coil 12 and resistance thermometer 21 are electrically insulated with a double polyurethane coating which melts during the soldering process. These fine wires cannot stand even extra fine sandpaper to remove the conventional enamel insulation.

Platinum wires were used for thermometer winding 15 in order to obtain high resistance. Copper may also be used in a resistance thermometer but the resistance is too low for short windings. In a left ventricular catheter with long resistance thermometers in the aorta either platinum or copper wires may be used, each with its own temperature coefficient of resistivity, since the thermometer does not move with each heart beat. Platinum has a high strain coefficient of resistivity but strain errors can be eliminated. Two types of errors are caused by strain phenomena in thermometer material.

The first type of error is strain caused by winding and coating of the thermometer during the making of the catheter. This source of error is corrected by measuring the new temperature coefficient of the resistance thermometer, that is, finding the resistance of the thermometer at the 0° C. point and at 100° C.

The second type of strain error is caused by the rhythmic movements of the thermometer with heart beats and the change in O.D. of the catheter caused by changing pressures of systole and diastole during the measuring time. These rhythmic movements of the catheter and changes in its O.D. affect the strain coefficient of resistivity of the wound thermometer. At rest these movements are repetitive and cause almost identical waves which may be filtered. However, during exercise the body movements and deep respiratory movements are reflected on the base line with irregular waves and affect the accuracy of each measurement. Use of a double spiral thermometer winding overcomes this problem.

The length and number of strands of heating coil winding 12 and platinum resistance thermometer winding 21 will vary with the size of the catheter. The length of heating coil 12 on the internal jugular catheter varies from 4 to 5 centimeters (2-3 centimeters for pediatrics) and the range of the length of resistance thermometer winding 21 is 5 to 7 centimeters (4 centimeters for pediatrics). The heating coil 12 for the left ventricular catheter should be around 7 cms. The resistance thermometer 21 should be 15-20 cms. long since it will be located inside the thoracic and abdominal aorta. These windings on the catheter are made with a weaving machine as it is known in the art.

The length and number of strands of fine wires used in winding of heating coil 12 and resistance thermometer 21 should be selected according to: (1) the site from which it is introduced to reach the regional blood flow to be measured, and (2) size of the patient or experimental animal. The length of heating coil 12, resistance thermometer 21 and distance between them depends on the expected range of the minute volume of blood flow at the site. Thus, catheters of several sizes and lengths, each for its own expected range of blood flow measurement may be needed.

When the catheter is introduced through one of the tributaries of the antecubital vein to reach the internal jugular vein, the overall length of catheter should be 110 cms. Catheters designed to measure left ventricular blood flow are introduced through one of the femoral arteries and therefore should be 125 cms long. These two lengths, 110 & 125, are standard lengths of conventional cardiac catheters.

The ratio of the surface area of the length and number of strands used to volume flow must be considered in establishing the heating coil and resistance thermometer lengths. For example, in the present invention for the study of blood flow in the internal jugular vein, the flow is about 400 ml/min. This compares to 4000-12000 ml/min. for cardiac output. Using the equation for the area of a cylinder, $2\pi rh$, where, $\pi$ equals $3,1416\ldots$, r is the radius of the catheter body 11 in nm, and h is the length of the windings in mm, and the above given lengths for heating coil 12 and resistance thermometer 21 along with an outside diameter of 1.5 mm, the surface area to volume flow ratio may be computed.

The resistance (and impedance) of heating coil 12 is always kept at a predetermined level by reducing or increasing the number and length of the wires used in parallel, to suit the range of blood flow to be measured. An impedance of 50 ohms was selected for use with the present invention because high frequency power and 50 ohms impedance coaxial cables were employed.

The volume of blood flow, which is directly proportional to the rate of heating and inversely proportional to temperature rise is obtained from the following formula $$\text{Volume flow} = \frac{W \times 0.239 \times 60}{0.92 \times T}$$

Where:
W is the predetermined rate of high frequency power in Watts, which is supplied to heater 12 or dummy load 36.
0.239 is the conversion factor from watts to calories,
60 is the conversion factor to obtain the minute volume,
0.92 is the product of specific heat (0.87) & density (1.056) of the blood,
T is the rise of the mean temperature of blood flowing through the vein or artery.

An advantage in having a constant predtermined heating coil resistance is that it allows for a direct milliliter per minute reading in direct readout recorder 39. This is accomplished by taking the above blood flow equation and substituting $V^2/R$ for W, where $V^2$ is the square of the voltage applied to heating coil 12 and R is the heating coil resistance. Because R is now 50 ohms the equation simplifies to:

$$\text{blood flow milliliters per minute} = V^2/T \times 0.311$$

Where:
$V^2$ = Square of the voltage applied to heater 12; and
T = rise of mean temperature of blood flowing through the blood vessel.

Since the applied voltage and temperature rise are readily available, the blood flow can be directly computed inside the apparatus and a direct readout in milliliters per minute made available. This is done by including analog multipliers inside recorder 39 to square the applied voltage, divide by the observed temperature rise, and multiply by the 0.311 constant. Direct readout provides a significant advantage over prior devices in that it makes data available more quickly and avoids computation errors.

Continual measurements of blood flow within a few seconds using this invention offers a number of other advantages. For example, each measurement can be carried out without the injection of any substance into the blood stream. Other thermodilution measurements made in man and in experimental animals have utilized a saline injection during each measurement. These injections are likely to increase cardiac output during the measuring period, and the error is further enlarged when the minute volume is calculated. Furthermore, the flexible connections to the subject allow the application of heat and measurement of temperature rise with ease and without sacrifice of accuracy. It is also possible to apply heat by remote control and obtain the signal indicative of temperature rise by telemetry.

Many modifications and variations of the present invention are possible in light of the above teachings. For example, this invention may also be used to measure the left ventricular output when catheter 11 is introduced through the femoral artery so that heating coil 12 is in the left ventricle while resistance thermometer 21 is in the aorta (FIG. 5). The base line indicating the temperature in the arterial system and left ventricle is far more stable than in the venous system, right ventricle or pulmonary arteries. This is because, in the venous syytem, right ventricle, and pulmonary arteries, the blood is not thoroughly mixed before reaching the lungs and its temperature is affected by respiration. Once the blood passes through the lungs however, the process of mixing is complete and the temperature of blood in the left atrium, left ventricle and arteries is constant, giving a stable baseline. With a stable temperature baseline from the aorta, a rate of heating ranging between 5–8 watts is all that is required to measure the left ventricular output.

It is therefore understood that within the scope of the disclosed inventive concept, the invention may be practiced otherwise than specifically described.

What is claimed is:

1. A bioelectric measuring apparatus for insertion within a living organism comprising:
   an elongated, flexible, catheter body having a distal or tip end and a proximal segment;
   main heating means, mounted on the distal or top end of said catheter body, for tepefying the surrounding substance of said living organism;
   temperature measuring means, mounted on the proximal segment of said catheter body, for quantifying the amount of caloric energy conducted to the surrounding substance of said living organism; and
   auxiliary heating means, electrically connected to said main heating means by lead wires, for providing heat to said lead wires.

2. A bioelectric measuring apparatus for insertion with a living organism according to claim 1 wherein said main heating means is a bifiliary wound heating coil.

3. A bioelectric measuring apparatus for insertion within a living organism according to claim 1 wherein said temperature measuring means comprises a platinum resistance thermometer.

4. A bioelectric measuring apparatus for insertion within a living organism according to claim 1 wherein said auxillary heating means comprises;
   a heating coil detached from said body for heating said lead wires; and
   switching means, electrically connected to said main heating means and said heating coil for selectively supplying current to either said main heating means or said heating coil.

5. A bioelectric measuring apparatus for insertion within a living organism according to claim 5 wherein said heating coil comprises a bifilarlywound coil with an impedance identical to that of said main heating means.

6. A bioelectric measuring apparatus for insertion within a living organism according to claim 4 wherein said switching means comprises a double pole double throw switch.

7. A bioelectric measuring apparatus for insertion within a living organism according to claim 1 further comprising
   conducting means, mounted on said body, for electrical contact with said living organism; and
   temperature transducing means mounted on said body, for sensing the temperature of said body produced by said main heating means.

8. A bioelectric measuring apparatus for insertion within a living organism according to claim 7 wherein said conducting means comprises one or more electrodes.

9. A bioelectric measuring apparatus for insertion within a living organism according to claim 8 wherein said electrodes comprise bare platinum electrodes.

10. A bioelectric measuring apparatus for insertion within a living organism according to claim 7 wherein said temperature transducing means comprises;

a thermocouple positioned along said main heating means; and a reference thermocouple positioned proximally to said main heating means.

11. A bioelectric measuring apparatus for insertion within a living organism according to claim 10 wherein said thermocouples are copper constantan thermocouples.

* * * * *